United States Patent [19]
Garcia Nunez

[11] Patent Number: 5,783,604
[45] Date of Patent: Jul. 21, 1998

[54] GERMICIDAL COMPOSITIONS CONTAINING IODINE COMPOUNDS

[76] Inventor: Maria Rosalia Garcia Nunez, Porto Cristo 10, Alcorcon, Spain, 28924

[21] Appl. No.: 762,729

[22] Filed: Dec. 10, 1996

Related U.S. Application Data

[63] Continuation-in-part of Ser. No. 399,807, Mar. 7, 1995, abandoned, which is a continuation-in-part of Ser. No. 907,869, Jul. 2, 1992, abandoned.

[51] Int. Cl.$^6$ ............................ A01N 33/12; A01N 37/18
[52] U.S. Cl. ............................................ 514/627; 514/643
[58] Field of Search ............................ 514/627, 643

[56] References Cited

U.S. PATENT DOCUMENTS

| | | | |
|---|---|---|---|
| 2,459,062 | 1/1949 | Cook et al. | 514/625 |
| 4,042,368 | 8/1977 | Argiriardi | 71/67 |
| 4,192,894 | 3/1980 | Botre et al. | 424/329 |
| 5,030,659 | 7/1991 | Bansemir et al. | 514/643 |

FOREIGN PATENT DOCUMENTS

| | | |
|---|---|---|
| 333976 | 12/1976 | Austria . |
| 0252310 | 1/1988 | European Pat. Off. . |
| 91/15120 | 10/1991 | WIPO . |
| 93/00813 | 1/1993 | WIPO . |

OTHER PUBLICATIONS

C. Ezpeleta et al., "Estudio Multicéntrico de la actividad antibacteriana de un nuevo disinfectante," *Revisita Espanõla de Quimioteropia*, Junio 1995, vol. 8 (2): 118–124.

English translation of C. Ezpeleta el al., "Estudio Multicéntrico de la actividad antibacteriana de un nuevo disinfectante," *Revisita Espanõla de Quimioteropia*, Junio 1995, vol. 8 (2): 118–124.

R. Cisterna and C. Ezpeleta, "Debemos evaluar la eficacia de los desinfectantes?", *Revisita Espanõla de Quimioterapia*, Junio 1995, vol. 8 (2): 97–99.

English translation of R. Cisterna and C. Ezpeleta, "Debemos evaluar la eficacia de los desinfectantes?", *Revisita Espanõla de Quimioterapia*, Junio 1995, vol. 8 (2): 97–99.

*Primary Examiner*—Allen J. Robinson
*Attorney, Agent, or Firm*—Kirkpatrick & Lockhart LLP

[57] ABSTRACT

Germicidal compositions containing iodine compounds with formulae I and II, where n is a whole number between 8 and 18. These compositions may include other chemical compounds which have a sterilizing and disinfecting function and which synergize and improve the activity of said compounds I and II. These germicidal compositions can be used, for example, for preventing infections in hospitals as well as in the food canning, pharmaceutical and other related industries.

3 Claims, No Drawings

GERMICIDAL COMPOSITIONS CONTAINING IODINE COMPOUNDS

This is a continuation-in-part application of U.S. application Ser. No. 08/399,807, filed Mar. 7, 1995, now abandoned, which is a continuation-in-part of U.S. application Ser. No. 07/907,869, filed Jul. 2, 1992, also now abandoned.

BACKGROUND OF THE INVENTION

1. Field of the Invention

The invention refers to a germicidal composition comprising two iodine compounds having different and specific functions in order to carry out a sterilizing and disinfecting activity or to synergize and improve the main effect of the active iodine compounds.

Said iodine compounds have a complex structure and include some high molecular weight molecules in which iodide has been fixed by means of a shifting reaction.

In particular, the iodine compounds used in the germicidal composition provided by the invention may correspond to the following general formulas: a) alkyl-dimethyl-benzyl-ammonium iodide (compound I), also named benzalkonium iodide, having the following general formula:

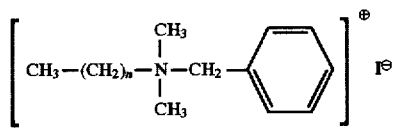

where n is a whole number between 8 and 18 (both included), and b) N-1-(3-trimethylammonium)-propyl undecylenamide iodide (compound II), also named 1-propanaminium,N,N,N-trimethyl-3-[(1-oxoundecenyl) amino, iodide, having the following general formula:

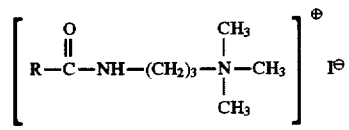

2. Use of the Invention

The germicidal compositions provided by the invention are suitable for preventing hospital infection, their main activity being to avoid and to control said infection which frequently arises during hospital practice, for example as post-surgical complication or by any other means, thus reducing death rates for these causes and reducing hospital costs.

In addition, germicidal compositions of the present invention may be used in industry, in particular in the food canning and in the pharmaceutical industries.

BACKGROUND ART

Hospital infection can be transmitted by different ways and can affect any person in a hospital. Not only patients, but also the hospital personnel and even the visitors may be affected by infection. The problem is hard to solve and very important. According to Mr. William Foege, 9% of all the American patients which have to stay in hospitals are infected by hospital infections not directly related with the original cause for going to the hospital. The increase in sanitary costs is also very relevant.

Hospital tests carried out with the germicidal compositions provided by the invention lead to results which allow one to conclude that the problem of infection can be satisfactorily solved by using said germicidal compositions.

PCT application published under publication number WO93/00813 discloses an alkyldimethylbenzylammonium iodide with a quaternary ammonium decylenic amide iodide to disinfect surfaces and further discloses a compendium of the state of the art in connection with systems and agents which may be used against microorganisms, which teachings are hereby incorporated herein by reference.

In general, none of the physical or chemical systems presently used in disinfection or sterilization properly solves the problems arising during disinfection processes and many of them present, in addition, limitations to their use. However, by using the germicidal compositions of the present invention it is possible to solve the mentioned problems and to properly disinfect all type of rooms and equipments.

DETAILED DESCRIPTION OF THE INVENTION

The germicidal compositions of the present invention comprise the above mentioned iodine compounds of formulas I and II:

a) alkyl-dimethyl-benzyl-ammonium iodide (compound of formula I) having the following general formula:

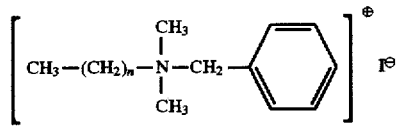

where n is a whole number between and 8 and 18 (both included) and b) N-1-(3-trimethylammonium)-propylundecylenamide iodide (compound of formula II) having the following general formula:

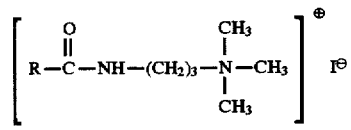

wherein R is a decylenic group. A decylenic group is an alkylenyl group having 10 carbon atoms with a double bond in any position of the group.

The compound of formula I could be obtained from the corresponding chloride by reaction with metallic iodine thereby causing a shifting of chlorine by iodine. Compound II can be obtained from the reaction of undecylenamidopropyltrimethylammonium methosulfate with metallic iodine, which causes a displacement of the methyl sulphate group by the iodine. The corresponding amide of the undecylenic trimethylammonium methosulfate acid can be obtained from the reaction of undecylenic acid with dimethylpropylendiamide followed by quaternization with dimethyl sulfate. A more detailed description of this process will be given when reviewing the preparation process of the germicide compositions of the present invention.

The germicidal compositions of the present invention are suitable for sterilizing and disinfecting rooms, equipment and apparatus. The chemical substances which can be present in the compositions together with the iodine compounds I and II are the following:

undecylenic acid diethanolamide;

an oxyethylenated fatty alcohol;

glycerol in order to avoid the astringent action of eventual free iodine in the composition;

a monoglyceride of oxyethylenated fatty acid in order to decrease the surface tension of the environment, thereby achieving a rapid humectation of the cell walls in the case of bacteria or breaking the different proteins which form the virus capsid; and a glycol in order to avoid the reaction of free iodine with other components of the germicidal composition.

An example of the undecylenic acid diethanolamide is that marketed under the commercial trade name EMPILAN UDE. This compound may be present in the germicide composition in a quantity approximately equal to 10–15% by weight, compared to the total weight of the composition.

The oxyethylenated fatty alcohol may be, for example, an alcohol ethoxylate having, for example, 8 moles of ethylene oxide, i.e., an alcohol with 12 to 20 carbon atoms which contains 8 epoxy groups in any position of the molecule. Examples of these compounds, but not limited thereto, are those marketed by the Companies ICI, PULCRA, KAO and REWO under the commercial trade names Synperonic A7/A9, Pulcra KQ33/KQ20, Findet 1618/1315/20 and Rewopal LA3/TA11, respectively. This compound can be present in a germicide composition in a quantity between 10–20% by weight, compared to the total weight of the composition.

The monoglyceride of an ethoxylated fatty acid is a compound formed by one molecule of glycerol which has one of its hydroxyl groups esterified with the remainder of a fatty acid of 12 to 20 carbon atoms which contain 4 to 8 oxyethylenated groups in any acceptable position in the molecule. Examples of these compounds, but not limited thereto, are those marketed by the companies KAO, REWO and PULCRA under the commercial trade names Findet OR/16/22, Rewoderm L1 420/ES90 and Pulcra KC11/LC10, respectively. This compound can be present in a germicide composition in a quantity between 5–10% by weight, compared to the total weight of the composition.

The glycerol, or 1,2,3-trihydroxypropane [$HOCH_2$—$CH$(OH)—$CH_2OH$], can be present in the germicide composition in a quantity approximately equal to 4–10% by weight, compared to the total weight of the composition.

The glycol may be hexylenglycol and can be present in the germicide composition in a quantity approximately equal to 10–15% by weight, compared to the total weight of the composition.

In a preferred embodiment of the present invention a germicidal composition is provided comprising:

benzalkonium iodide (compound I) . . . 35–50%, preferably 38.5%

N-1-(3-trimethylammonium-propyl-undecylenamide iodide (compound II) . . . 3–10%, preferably 4.5%

All the proportions are indicated in weight percentages of the total weight of the composition. As can be seen, the preferred form of the product provides a germicide composition which includes (a) benzalkonium iodide in a proportion of approximately 38.5% by weight, compared to the total for the germicide composition, and (b) N-1-(3-trimethylammonium)-propyl-undecylenamide iodide in a proportion of approximately 4.5% by weight compared to the total for the germicide composition.

The germicidal compositions of the present invention may be obtained by a process comprising the following steps:

a) loading a reactor provided with stirring means with the appropriate amounts of previously melted benzalkonium chloride;

b) adding while smoothly stirring the appropriate amount of N-1-(3-trimethylammonium)-propyl-undecylenamide methyl sulfate;

c) adding the appropriate amount of hexylenglycol;

d) slowly adding sublimated metallic iodine in the appropriate stoichiometric proportion while increasing the stirring;

e) adding the appropriate amounts of:
   i) monoglyceride of oxyethylenated fatty acid;
   ii) glycerol;
   iii) oxyethylenated fatty alcohol with 8 moles of ethylene oxide; and
   iv) undecylenic acid diethanolamide; and f) adding inorganic acid until a pH of approx. 4.5 is obtained.

In general, the process is carried out at a temperature slightly over 20° C., the stirring speed being in the range of between 400 and 1600 rpm.

By this way of operation, the shifting of the chloride and the methyl sulfate groups of the reacting substances and their substitution by iodine is achieved, the above mentioned iodine derivatives I and II being formed thereby.

It has been stated that the germicidal compositions provided by the present invention perform their activity by the following mechanism:

extraction of essential cellular metabolites;

denaturation of cellular proteins;

reaction with cellular lipids;

provoking an enzymatic disequilibrium and inhibiting essential coenzymes for the microorganisms; and expulsing the vital matter out of the cell through the membrane by disrupting the osmotic balance.

This mechanism enables the germicidal compositions provided by the present invention to be very effective, not only against Gram-positive and Gram-negative bacteria, but against Mycobacteria and viruses as well and therefore they can be used for sterilizing and disinfecting rooms, equipment, apparatus, etc.

It has been stated that the germicidal compositions provided by the present invention, in particular the previously mentioned preferred composition, is not an irritant, is not sensibilizing and is non-mutagenic at the dosages tested. This is illustrated by examples 5 to 7. The composition is very effective against different types of germs, such as bacteria (Examples 2, 4 to 9, and 11), fungi (Examples 2, 4 and 10) and yeast (Example 2). In addition, the germicide composition provided herein exhibits a sporicide effect on spores of *Bacillus subtilis* (Example 8). In addition, Example 12 illustrates the capability of the germicide composition for environmental microbiological control in an injection room and in a lyophilization room at a pharmaceutical laboratory.

Example 13 shows that the germicidal composition provided by this invention is more efficient than two other currently used germicidal compositions (persulfate and glutaraldehyde) in disinfecting endoscopes by an assay of the true efficiency with controlled contamination.

Any expert in this field, having read the present description, will note that the essence of the synthesis of the germicide compositions of the invention lies in the displacement and substitution of the chloride present in benzalkonium chloride by an iodide, and in the displacement and substitution of the methyl sulfate group present in N-1-(3-trimethylammonium)-propyl-undecylenamide methyl sulfate by an iodide. It is believed that the germicidal, bactericidal and fungicidal activity of compounds (I) and (II) provided by this invention is due to the association of the iodides.

All the other possible modifications like the substitution of the benzyl group of compound I by other aromatic groups, as well as variations in the number of —$CH_2$— groups and their arrangement (lineal or branches), are secondary changes which do not affect the germicidal or fungicidal activity of compounds I and II of the present invention.

Following, some examples of different ways of carrying out the process of the invention are given, as well as some other examples illustrating the germicidal activity of the considered compositions. Said examples do not limit the scope of the present invention.

EXAMPLE 1

A stainless steel reactor provided with stirring means is loaded with 384 g of previously melted benzalkonium chloride. Stirring is then started at a speed of 500 rpm and 45 g of N-1-(3-trimethylammonium)-propyl-undecylenamide methyl sulfate are then added at a temperature over 20° C. Stirring is maintained until a complete mixture of all the components is achieved, approximately after 10 minutes. Later, 128 g of hexylenglycol are added while maintaining the same stirring and temperature conditions until complete mixing. 35 g of sublimated metallic iodine are then added very slowly while the stirring speed is increased up to 1500 rpm. Stirring is maintained until iodine is completely dissolved and has reacted with the other components. The final mixture should not have suspended particles.

The following compounds are then added to the obtained mixture:

i) 128 g of undecylenic acid diethanolamide;

ii) 177 g of oxyethylenated fatty alcohol with 8 moles of ethylene oxide;

iii) 47 g of glycerol; and iv) 54 g of the monoglyceride of the polyoxyethylenated fatty acid.

Stirring is maintained for at least 15 minutes and finally a mineral acid is added until the resultant solution reaches a pH of approx. 4.5. Stirring is maintained for one hour. After checking that no residues of free iodine are present, the obtained composition can be bottled.

| | |
|---|---|
| Benzalkonium iodide | 38.5% |
| N-1-(3-trimethylammonium)-propyl-undecylenamide iodide | 4.5% |
| Oxyethylenated fatty alcohol with 8 moles of ethylene oxide | 18% |
| Ethoxylated fatty acid monoglyceride | 6% |
| Glycerine | 5% |
| Hexylenglycol | 13% |
| Undecylenic acid diethanolamide | 13% |
| Phosphoric acid sufficient in quantity to maintain pH of 4.5 | |

EXAMPLE 2

Test of Effectiveness against Different Types of Germs

Some microbiological tests were carried out for determining the microbicidal activity of the composition obtained according to Example 1. Three different types of microorganisms were tested: bacteria, yeast and fungi.

A bouillon made of meat and glucose yeast was used as culture medium and the germs used were:

i) 128 g of undecylenic acid diethanolamide;

ii) Staphylococcus aureus;

ii) Saccharomyces ellipsoideus; and iii) Penicillium crysogenum.

The following consecutive dilution technique was used: 1, 5, 10, 20, 50, 100, and 200 ppm. 48 hour cultures of the germs indicated above were inoculated (0.01 $cm^3$ in each case). The growth measurements were made by nephelometry.

In a second set of tests different dilutions were used interpolating the doses between those of the first experiment where growth was first detected. Finally, the germicide activity was tested by viability culture in an agar environment. The following results were obtained:

FIRST EXPERIMENT

| Germ | Germicide Activity (no growth) Dose between (ppm) |
|---|---|
| Staphylococcus aureus | 1 and 5 |
| Saccharomyces ellipsoideus | 10 and 20 |
| Penicillium crysogenum | 20 and 30 |

SECOND EXPERIMENT

| Germ | Microbicidal activity (ppm) | One part in |
|---|---|---|
| Staphylococcus aureus | 3 | 333.333 |
| Saccharomyces ellipsoideus | 12 | 85.333 |
| Penicillium crysogenum | 22 | 45.000 |

These results indicate the microbicidal effect of the germicidal compositions of Example 1 against the tested germs.

EXAMPLE 3

Test of Antimicrobial Activity in Drinking Water

A test was carried out for determining the antimicrobial activity of the compositions obtained according to Example 1 in relation to microorganisms contained in drinking water. The test was carried out according to the Swiss norm Clinical Microbiology ASM 1991 which briefly comprises:

a) diluting the germicidal composition in sterile deionized water;

b) homogenizing 10 ml of a drinking water sample and 10 ml of the diluted germicidal composition in a vibrating device; and c) maintaining the mixture in contact during 15 minutes and transferring 1 ml of said sample to 10 ml of Muller-Hinton gel heated at 45° C. and immediately transferring it to a culture plate. Simultaneously, 1 ml of the water-germicidal composition is transferred to 1 ml of double concentrated Muller-Hinton gel. The obtained preparations were incubated at 37° C. for 24 hours.

The following results were obtained:

1. Microbiological test of the drinking water used 1.1 Number of germs per ml: 407.5

1.2 Isolated germs:
Pseudomonas putida
Xanthomonas maltophilia
Streptococcus
Chromobacter

7

*Staphylococcus coagulase*
*Bacillus sp*
*Aspergillus niger*
*Aspergillus sp*

2. Antimicrobial power Dilutions of the germicide composition

| | $10^{-2}$ | $5 \times 10^{-2}$ | $10^{-3}$ | $2.5 \times 10^{-3}$ | $5 \times 10^{-3}$ | $10^{-4}$ | $1.5 \times 10^{-4}$ |
|---|---|---|---|---|---|---|---|
| Growth | − | − | − | − | − | + | + |

From the obtained results it can be stated that the germicidal composition can be used for decontaminating drinking water at a dilution between 1/2500 and 1/5000.

EXAMPLE 4

Test of Effectiveness against Different Microorganisms

In this Example, the effectiveness, i.e., the disinfectant capability, of the germicide obtained in Example 1 against various microorganisms (bacteria and fungi) was evaluated. Two different tests were conducted to illustrate this.

4.1 First test

The effectiveness of the germicide composition was evaluated in the first test against:

a) bacteria: species of *Salmonella spp.*, *Staphylococcus aureus*, *Pseudomonas aeruginosa*, *Escherichia coli*, and b) fungi: *Candida albicans* and *Aspergillus niger*

In this first test, the germicide composition was tested at concentrations of 3/1000 and 9/1000. Distilled water was used as a diluent for the germicide compound in this test and in all other tests, except where indicated otherwise.

Starting with the test samples of the different microorganisms mentioned above, the corresponding microbial suspensions were prepared containing $10^7$ colony forming units/ml ("cfu/ml").

The microbial suspensions thus prepared were placed in contact with the different concentrations of the germicide composition (3/1000 and 9/1000) for contact times of 1, 3, and 5 minutes. At each of the times indicated, samples were removed and cultured on the proper liquid cultivation media for each case and subsequently incubated at the proper temperatures and conditions for each microorganism. Then, after the incubation period was over, the liquid media were placed on solid cultivation media suitable for each microorganism in order to verify the presence or absence of growth of the microorganism in question.

In all cases, an absence of growth was observed for the two concentrations and for the three contact times studied.

As such, these results demonstrate that the germicide composition of Example 1 is effective, i.e., has disinfectant capability, against *Salmonella spp.*, *Staphylococcus aureus*, *Pseudomonas aeruginosa*, *Escherichia coli*, *Candida albicans* and *Aspergillus niger* at concentrations of 3/1000 and 9/1000 and at contact times of 1, 3, and 5 minutes.

4.2 Second test

In a second test, the effect of the germicide composition against the strains of bacteria and fungi which appear in Table 1 below was evaluated.

8

In this second test, three dilutions of the germicide compound were evaluated (1/10, 1/100 and 1/1000).

The tests to verify the effect of the action of the germicide compound were determined by radial diffusion on plates. For this, the plates were inoculated with the microorganism in question and the different dilutions of the germicide product were dispensed in wells over the seeded surface of the plate. 100 μl of each dilution of the germicide composition was added to each well. The plates were incubated for 24–48 hours at a temperature suitable for the growth of each microorganism, at the end of which time the diameters of the inhibition halos resulting from the action of the germicide composition against the different microorganisms were measured.

TABLE 1

| | Germicide Composition Dilutions | | |
|---|---|---|---|
| Strain | 1/10 | 1/100 | 1/1000 |
| *Bacillus cereus* | + | + | + |
| *Staphylococcus aureus* MARSA | + | + | + |
| *Staphylococcus aureus* CECT4439 | + | + | + |
| *Pseudomonas fluorescens* | + | + | + |
| *Salmonella typhirmurium* | + | + | + |
| *Escherichia coli* | + | + | + |
| *Candida albicans* | + | + | + |
| *Cryptococcus albidus* | + | + | + |
| *Aspergillis nidulans* | + | + | + |

A positive ("+") result was recorded in Table 1 when the inhibition halos were greater than or equal to the result obtained using disks of 10 U.I. of penicillin against *Bacillus subtilis* for a dilution of 1/10 and the result obtained using 2 U.I. for lower dilutions.

EXAMPLE 5

Study on Disinfectant Capability against *Bacillus subtilis*

The disinfectant capability of the germicide composition obtained in Example 1 against a strain of *Bacillus subtilis* was evaluated in this study.

The germicide composition was tested at concentrations of 1/1, 1/2, 1/4, 1/6, and 1/10 for this study.

A microbial suspension containing $5 \times 10^8$ cfu/ml was prepared from a strain of *Bacillus subtilis*.

The microbial suspension was then placed in contact with the different concentrations of germicide composition mentioned previously for different contact times (1, 3, and 5 minutes). Aliquots were extracted at each of the times indicated and seeded on soy tryptone broth. Then, the different soy tryptone broths, previously inoculated with each concentration of the I germicide composition and *B. subtilis*, were incubated at 35° for 48 hours. After this time had elapsed, the soy tryptone broths were transferred to plates to verify the presence or absence of growth of *B. subtilis*.

The results obtained are shown in Table 2.

TABLE 2

| | Disinfectant capability against Bacillus subtilis | | |
|---|---|---|---|
| | Time (minutes) | | |
| Germicide Composition | 1 | 3 | 5 |
| 1/1 | − | − | − |
| 1/2 | − | − | − |
| 1/4 | + | + | + |
| 1/6 | + | + | + |
| 1/10 | + | + | + |

"+" growth of microorganism
"−" absence of growth

These results clearly demonstrate that the germicide composition from Example 1 is effective against *Bacillus subtilis* at a minimum concentration of ½ for any of the time periods studied.

EXAMPLE 6

6.1 Study of bactericide capability

This study was conducted on a multi-resistant strain of *Staphylococcus aureus* (MARSA) maintained at the Department of Microbiology of the Faculty of Pharmacology of the University of Salamanca, Spain.

Two dilutions of the germicide compound from Example 1 were tested, specifically, 1/100 and 1/1000.

The microorganism was incubated in a liquid YED (yeast-agar glucose extract) medium with orbital agitation of 180 rpm until it reached between 2 and $5 \times 10^9$ cfu/ml.

The microorganism suspension was placed in contact with the two dilutions of the germicide composition for 15, 30 and 60 seconds. The recovery of viable bacteria was carried out on a plate containing YED medium.

The results obtained are shown in Table 3.

TABLE 3

| | Bactericide capability against Staphylococcus aureus | | |
|---|---|---|---|
| Concentration | 15 sec | 30 sec | 60 sec |
| 1/100 | — | — | — |
| 1/1000 | — | — | — |

"—" absence of growth 6.2 Study on bacteriostatic capability

This study was conducted on the multi-resistant strain of *Staphylococcus aureus* (MARSA) mentioned above.

Dilutions between 1/10 and 1/10$^7$ of the germicide composition from Example 1 were tested.

The test was conducted on a liquid YED (yeast-agar glucose extract) medium to which the microorganism was added from a culture which contained between 2 and $5 \times 10^8$ cfu/ml.

The culture media inoculated with the microorganism and containing the concentrations of the germicide composition mentioned above were incubated at 37° C. for 24 hours.

The minimum inhibiting concentration ("MIC") was considered to be the lowest concentration that inhibited bacterial growth, detectable by means of optical density ("OD").

According to the results obtained, the MIC of the germicide composition from Example 1 against the strain of *Staphylococcus aureus* (MARSA) was 1/10$^8$.

Subsequently, viable bacteria were recovered from the medium which contained this dilution on a plate containing YED medium, which indicates that the germicide compound is bacteriostatic at this concentration under the conditions used and against the bacteria tested.

EXAMPLE 7

Study of Disinfectant Capability against *Legionella pneumophila*

In this study, the disinfectant capability of the germicide composition obtained in Example 1 against a strain of *Legionella pneumophila* was tested.

The germicide composition was tested undiluted with a contact with the bacterial strain of 1, 3, and 5 minutes.

A microbial suspension containing $10^6$ to $10^9$ cfu/ml was prepared from a strain of *Legionella pneumophila*. The microbial suspension was placed in contact with the germicide composition for different contact times (1, 3, and 5 minutes). At each of the times indicated, aliquots were extracted, which were seeded on a plate containing BCYE medium. Then, the different inoculated plates were incubated at 37° C. in a humid atmosphere containing 10% $CO_2$.

The results obtained showed the absence of growth in all cases, without recovery of the inoculum. As such, these results clearly demonstrate that the germicide composition from Example 1 is effective, i.e., exhibits a disinfectant effect against *Legionella pneumophila* at a concentration of 100% for any of the time periods studied.

EXAMPLE 8

Determination of Sporicide Effect

This test was conducted to evaluate the possible sporicide effect of the germicide composition obtained in Example 1 against spores of *Bacillus subtilis*. Because these spores are very resistant to any type of physical or chemical sterilization procedure, they are frequently used as biological controls.

The procedure used is based on the method described by Dominguez Rojas et al. in L'Igiene Moderna, 95:654:661 (1991). Briefly, this method consists of impregnating endodontia limes (Triocut Heli-Filers 40) with vegetative forms of *Bacillus subtilis* ($5 \times 10^8$ cfu/ml) with inoculation medium and waiting until spores are formed. Then, the "germ carriers" are placed in contact with the germicide composition and subsequently, at specific times (5, 10, 15, 30, 60 minutes and 2, 4, 8, and 24 hours), the action of the germicide composition is stopped by adding a suitable inhibitor to the germicide composition. Finally the "germ carriers" are subcultivated to determine if any *Bacillus subtilis* has survived.

The results obtained demonstrate that the germicide composition tested has sporicide properties (sterilizing a "germ carrier" with spores of *B. subtilis*) at very short times (5–10 minutes).

EXAMPLE 9

Study of the MIC of the Germicide Composition against Different Pathogens

Following conventional procedures of microbiology, this study was conducted to determine the MIC of the germicide composition obtained in Example 1 against the microorganisms listed in Table 4. The MIC values are shown in that table, as well as the germicide composition concentrations tested.

11

TABLE 4

| Microorganism | MIC | Composition Concentration |
|---|---|---|
| *Proteus vulgaris* | 0.075% | 0.075% |
| *Proteus mirabilis* | 0.075% | 0.075% |
| *Proteus penneri* | 0.075% | 0.075% |
| Salmonella spp. | 0.0083% | 0.0083% |

EXAMPLE 10

Study of Fungicide Activity

This study was conducted to evaluate the fungicide activity of the germicide composition obtained in Example 1 against the fungi listed in Table 5.

The method followed was the dilution-neutralization method (AFNOR NF T 72–200 Standard), using the following experimental conditions:

Test temperature: 21°–22° C.

Preparation liquid for the suspensions of the spores of the fungi: Tween 80 Solution at 0.05%.

Neutralizer:

a) Composition per 100 ml P/V

| Glycine | 2% |
|---|---|
| Soy lecithin | 2% |
| Tween 80 | 2% |
| Distilled water, csp | 100% | b) Sterilization: Autoclave, 121° C., 20 minutes
c) Concentration: Pure in all cases Diluent of the germicide compound: Distilled water.

The results obtained are shown in Table 5, where the values of the fungicide concentrations of the germicide composition are shown. These results clearly demonstrate the fungicidal activity of the germicide composition.

TABLE 5

Fungicide activity

| Fungus | Fungicide concentration |
|---|---|
| *Penicillium verrucosum* | 1/200 |
| *Absidia corymbifera* | 1/100 |
| *Aspergillus niger* | 1/200 |
| *Candida albicans* | 1/3000 |

EXAMPLE 11

This test was conducted to evaluate the disinfectant capability of the germicide composition obtained in Example 1 against the microorganisms listed in Table 6 over time.

The concentration of the germicide composition tested was 3/1000.

From the strains indicated in Table 6, corresponding suspensions were prepared which contained approximately $10^8$ cfu/ml.

The suspensions thus prepared were placed in contact with the germicide composition for different contact times (1, 3, and 5 minutes). At each of the times indicated, aliquots were extracted which were seeded on appropriate culture media, specifically—for bacteria: soy tryptone broth [Trypticase Soy Agar, Merck 5458] and for fungi: Saboureaud dextrose agar [Saboureaud dextrose Agar, Merck 5464]. Then, the different broths were incubated at 37° C. for 48 hours. After this time, they were put on plates to verify the presence or absence of growth of the microorganisms.

The results obtained are shown in Table 6.

TABLE 6

| | Recovery of the inoculum | | |
|---|---|---|---|
| Strain | 1 min | 3 min | 5 min |
| *Escherichia coli* ATCC8739 | – | – | – |
| *Staphylococcus aureus* ATCC6538 | – | – | – |
| *Pseudomonas aeruginosa* ATCC9027 | – | – | – |
| *Salmonella enteritidis* | – | – | – |
| *Candida albicans* ATCC10231 | + | +/– | – |

"+": presence of growth (recovery of inoculum)
"+/–": presence of growth (certain recovery of inoculum)
"–": absence of growth (no recovery of inoculum)

The results obtained clearly demonstrate the following:

a) The germicide composition, at a dilution of 3/1000, exhibits bactericidal activity against the bacterial strains tested, with a contact time of 1 min; and b) The germicide composition, at a dilution of 3/1000, exhibits activity against the strain of C. albicans tested with a contact time of 5 minutes.

EXAMPLE 12

Environmental microbiological control study

This study was conducted to evaluate the environmental microbiological control of different areas for the production of sterile material after using the germicide composition from Example 1 for 10 minutes in each room. The rooms where the test was conducted were the injection room (40 m$^2$) and a lyophilization room (50 m$^2$), sampling only one point in each room.

The environmental control test was conducted by aspiration of air by centrifugal force onto agar strips on plates for bacteria and Saboureaud dextrose agar for fungi. The sampling was conducted for 2 minutes, followed by incubation at 30° C. for 48–72 hours and at 22° C. for 5–7 days, respectively.

The results obtained are shown in Table 7, which indicate the values before and after the use of the germicide composition.

TABLE 7

| | Environmental microbiological control | |
|---|---|---|
| Room Sample | Before addition of the germicide (Bacteria/fungi per unit volume) | After addition of the germicide composition (Bacteria/fungi per unit volume) |
| Injection | 6.25/0 cfu/m$^3$ | 0/0 cfu/m$^3$ |
| Lyophilization | 8.75/12.5 cfu/m$^3$ | 0/0 cfu/m$^3$ |

The results obtained demonstrate that the germicide composition from Example 1 is effective in environmental microbiological control.

EXAMPLE 13

Comparison of the Antimicrobial Efficiency of Different Germicidal Compositions

This example was conducted to compare the efficiency of the germicidal composition provided by this invention against two known germicides.

1. Materials:

1.1 Germicides:

[A]: 0.44% germicidal composition of Example 1 (50-fold diluted);

[B]: 2% glutaraldehyde (commercial product); and

[C]: 1% persulfate [VIRKON®, 1 gram in 99 grams of water].

1.2 Microorganisms:

42 microorganisms derived from patients of the Intensive Care Unit (22 Enterobacteriae, 8BNF, 8 Gram positive cocus and 4 yeasts);

2 Mycobacteriae; and 4 microorganisms belonging to the Bacillus genus (subtillis and cereus), transforming the vegetative cells into spores, by aging and further heating to destroy the vegetative cells remaining as such.

2. Methods:

2.1 Method in vitro

In order to carry out this assay in a reproducible way, plastic tubes of 1 mm diameter and 1 m long, similar to those of the endoscopes were used. Said tubes were firstly sterilized by fluent vapor and subsequently they were contaminated with 1 ml of a 24 hour culture of a microorganism by using a syringe and a needle. After 15 minutes, the tubes were put into different vessels each one containing a different germicide composition (A, B and C) and another one containing sterilized distilled water (control) for 10 minutes, except in the case of Mycobacteriae where two periods of time were considered (10 and 30 minutes). Subsequently, tubes were washed with 1 ml of sterilized distilled water (3×). A 0.1 ml sample from said effluent was inhibited with 0.9 ml of a suitable inhibitor (broth, 6% Tween 80, s0.5% sodium bisulfite and 0.5% sodium thiosulfite) and 2 samples of 0.1 ml were seeded in Mueller-Hinton plates which were incubated and the colony forming units (cfu) were counted and the reduction of microorganisms with respect to the control was calculated (5).

In the case of Mycobacteriae two different times were studied (10 and 30 minutes) and an intermediate disinfection-washing step was included (using 1 ml of the germicidal composition) before performing the disinfection treatment by immersion.

2.2 Effective conditions assay

The endoscopes were externally washed and immersed in the germicidal composition for 10 minutes, clarified with water and dried by pumping or aspiration. 0.1 ml from the clarified water were seeded. If no growth is observed after incubation, then 10 ml of broth are added and re-incubation is performed in order to multiply and identify the microorganisms present in the sample.

2.3 Statistics

Since populations did not follow a normal distribution, non-parameters assays were carried out (U-Mann-Whitney).

3. Results 3.1 The average number of microorganisms inside each tube was 3,900,000 (Sm=426,000). The overall analysis of the 48 microorganisms with the different germicidal compositions shows that the efficiency of germicidal composition [A] is higher than those of compositions [B] and [C] (which efficiency is very similar) as shown in Table 8. This may be due to the direct efficiency of composition [A] on the microorganisms and by its penetration ability due to a lower tension surface.

TABLE 8

Comparative effect (immersion 10 minutes) of 3 germicidal compositions over 48 microorganisms, in an endoscope model with controlled contamination

| Composition | Surviving (%) |
|---|---|
| A | 0.9 |
| B | 2.9 |
| C | 2.6 |

3.2 By groups of microorganisms, the above mentioned results are repeated. Thus, in Gram negative bacteriae (GNB) and spores, less than 0.1% survive after treatment with composition, whereas with the other two compositions, the number of surviving microorganisms is 2- or 4-fold higher, as mentioned in Table 9. Composition A is also the most efficient germicidal composition against Gram positive bacteriae (GPB) and yeasts.

TABLE 9

Comparative effect (immersion 10 minutes) of 3 germicidal compositions over 46 microorganisms, in an endoscope model with controlled contamination

| Composition | Microorganisms | Surviving (%) |
|---|---|---|
| A | GNB | 0.9 |
|   | GPB + yeasts | 0.6 |
|   | spores | 1.9 |
| B | GNB | 2.3 |
|   | GPB + yeasts | 1.7 |
|   | spores | 4.4 |
| C | GNB | 3.7 |
|   | GPB + yeasts | 1.3 |
|   | spores | 3.7 |

3.3 With Mycobacteria, two different times 10 and 30 minutes) and two different conditions with and without prior washing/disinfection). Table 10 shows that the reduction in the surviving microorganisms is not very high at 20 minutes although is higher at 30 minutes. The reduction is increased with washing.

TABLE 10

Comparative effect (immersion 10 or 30 minutes, with or without prior washing) of 3 germicidal compositions over Mycobacterium fortuitus in an endoscope model with controlled contamination

| Composition | Conditions | Surviving (log decimal) |
|---|---|---|
| A | no washing, 10 min | 4.0 |
|   | no washing, 30 min | 3.3 |
|   | washing, 10 min | 0.8 |
|   | washing, 30 min. | 0.3 |
| B | no washing, 10 min | 4.1 |
|   | no washing, 30 min | 3.3 |
| C | no washing, 10 min | 4.4 |
|   | no washing, 30 min | 3.4 |
|   | washing, 10 min | 1.2 |
|   | washing, 30 min | 1.1 |
| Control | no washing, 10 min | 4.3 |
|   | no washing, 30 min. | 4.6 |
|   | washing, 10 min | 2.6 |
|   | washing, 30 min | 2.6 |

3.4 Table 11 shows the good real efficiency of composition [A] since it was capable to disinfect, under use conditions, an endoscope with a controlled contamination (0 surviving microorganisms). It is also shown that with a high contamination (>10%), after the washing/disinfection step, the microbial charge is reduced more than four logarithm units.

TABLE 11

Comparative effect (immersion 10 or 30 minutes, with or without prior washing) of composition A over 4 microorganisms in an endoscope model with controlled contamination

| Composition | Microorganisms | Surviving (log decimal) |
|---|---|---|
| A | Escherichia coli | 0 |
|  | Escherichia faecalis | 0 |
|  | Candida | 0 |
|  | Pseudomonas | 0 |
| Control | Escherichia coli | 3.6 |
|  | Escherichia faecalis | 3.2 |
|  | Candida | 3.1 |
|  | Pseudomonas | 4.0 |
| Control without washing | Escherichia coli | 8.4 |
|  | Escherichia faecalis | 8.2 |
|  | Candida | 7.0 |
|  | Pseudomonas | 8.6 |

Therefore, the germicidal composition of the invention [A] is a very effective disinfectant of endoscopes, even better than 2% glutaraldehyde which is the disinfectant of reference for said devices.

What is claimed is:

1. A germicide composition comprising:
   a) 35–50% by weight compared to the total composition weight of alkyl-dimethyl-benzyl-ammonium iodide, having the formula:

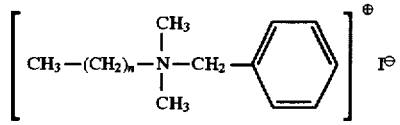

where n is a whole number between 8 and 18 (both included);
   b) 3–10% by weight compared to the total composition weight of N-1-(3-trimethylammonium)-propyl-undecylenamide iodide, having the following formula:

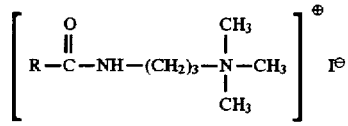

where R is a decylenic group; and
   c) the remaining 40–62% by weight comprising:
   undecylenic acid diethanolamide;
   a fatty alcohol oxyethylenated with 8 moles of ethylene oxide;
   an oxyethylenated fatty acid monoglyceride;
   glycerine;
   hexylenglycol
   an inorganic acid in a quantity sufficient to provide a pH of 4.5.

2. A process for obtaining a germicide composition which comprises mixing at approximately 20° C. and with a stirring speed between 400 and 1600 rpm;

35–50% by weight of a previously molten benzalkonium chloride;

3–10% by weight of N-1(3-trimethylammonium)-propylundecylenamide methyl sulfate;

10–15% by weight of hexylenglycol;

sublimated metallic iodine in the stoichiometric amount to shift the chloride anion from the benzalkonium chloride and the methyl-sulfate group from the N-1-(3-trimethylammonium)-propyl-undecylenamide methyl sulfate;

10–15% by weight of undecylenic acid diethanolamide;

10–20% by weight of a fatty alcohol oxyethylenated with 8 moles of ethylene oxide;

5–10% by weight of an oxyethylenated fatty acid monoglyceride;

4–10% by weight of glycerine; and an inorganic acid to maintain a pH of 4.5, wherein all the proportions are compared to the total composition weight of the composition to be obtained.

3. A method for disinfecting a surface, the method comprising the step of applying an effective disinfecting quantity of a germicide composition to the surface, said germicide composition comprising:

a) 35–50% by weight compared to the total composition weight of an alkyl-dimethyl-benzyl-ammonium iodide having the following formula:

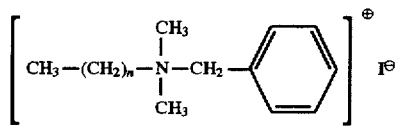

where n is a whole number between 8 and 18 (both included);
   b) 3–10% by weight compared to the total composition weight of N-1-(3-trimethylammonium)-propyl-undecylenamide iodide, having the following formula:

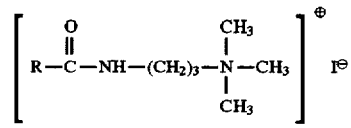

where R is a decylenic group; and
   c) the remaining 40–62% by weight comprising:
   undecylenic acid diethanolamide;
   a fatty alcohol oxyethylenated with 8 moles of ethylene oxide;
   an oxyethylenated fatty acid monoglyceride; glycerine;
   hexylenglycol; and
   an inorganic acid in a quantity sufficient to maintain a pH of 4.5.

* * * * *